(12) United States Patent
Ouchi

(10) Patent No.: US 7,402,162 B2
(45) Date of Patent: Jul. 22, 2008

(54) HIGH FREQUENCY TREATMENT INSTRUMENT FOR ENDOSCOPE

(75) Inventor: Teruo Ouchi, Saitama (JP)

(73) Assignee: Hoya Corporation, Tokyo (JP)

( * ) Notice: Subject to any disclaimer, the term of this patent is extended or adjusted under 35 U.S.C. 154(b) by 297 days.

(21) Appl. No.: 11/086,436

(22) Filed: Mar. 23, 2005

(65) Prior Publication Data

US 2005/0215996 A1  Sep. 29, 2005

(30) Foreign Application Priority Data

Mar. 24, 2004 (JP) ............................ 2004-085847
May 21, 2004 (JP) ............................ 2004-151268

(51) Int. Cl.
*A61B 18/18* (2006.01)
(52) U.S. Cl. ................ 606/45; 606/1; 606/46
(58) Field of Classification Search ...... 606/1, 606/13, 14, 23, 27–29, 32–52; 604/43–45; 600/104; 43/43.16; 348/65
See application file for complete search history.

(56) References Cited

U.S. PATENT DOCUMENTS

| | | | |
|---|---|---|---|
| 4,492,832 A | | 1/1985 | Taylor |
| 4,733,662 A | | 3/1988 | DeSatnick et al. |
| 5,057,107 A | * | 10/1991 | Parins et al. ............ 606/48 |
| 5,261,906 A | * | 11/1993 | Pennino et al. ........ 606/46 |
| 5,401,274 A | | 3/1995 | Kusunoki |
| 5,460,629 A | * | 10/1995 | Shlain et al. ............ 606/46 |
| 5,480,398 A | * | 1/1996 | Eggers ................... 606/29 |
| 5,891,141 A | * | 4/1999 | Rydell .................... 606/45 |
| 5,936,536 A | * | 8/1999 | Morris .................. 340/647 |
| 5,938,661 A | * | 8/1999 | Hahnen .................. 606/46 |
| 6,007,514 A | | 12/1999 | Nita |
| 6,190,384 B1 | * | 2/2001 | Ouchi .................... 606/47 |
| 6,478,794 B1 | * | 11/2002 | Trapp et al. ............ 606/45 |
| 6,730,081 B1 | * | 5/2004 | Desai .................... 606/40 |
| 6,808,525 B2 | * | 10/2004 | Latterell et al. ........ 606/42 |
| 7,060,065 B2 | * | 6/2006 | Ohyama et al. ........ 606/46 |
| 2003/0040744 A1 | * | 2/2003 | Latterell et al. ........ 606/48 |
| 2003/0130655 A1 | * | 7/2003 | Woloszko et al. ...... 606/45 |

(Continued)

FOREIGN PATENT DOCUMENTS

JP  6-292685  10/1994

(Continued)

OTHER PUBLICATIONS

English Language Abstract of JP 7-008503.

(Continued)

*Primary Examiner*—Michael Peffley
*Assistant Examiner*—Victoria W Chen
(74) *Attorney, Agent, or Firm*—Greenblum & Bernstein, P.L.C.

(57) ABSTRACT

A high frequency treatment instrument for an endoscope is provided. The high frequency treatment instrument is provided with an insulative flexible sheath, an operation wire inserted in the flexible sheath so as to be movable along an axial direction of the operation wire in the flexible sheath, and a hook-like electrode attached to a tip of the operation wire. The hook-like electrode includes a rod-like part which is elongated in parallel with the axial direction along a line shifted from an axis line of the operation wire, and a hook part elongated from the rod-like part to cross the axis line of the operation wire.

18 Claims, 15 Drawing Sheets

U.S. PATENT DOCUMENTS

| | | | |
|---|---|---|---|
| 2004/0019350 A1* | 1/2004 | O'Brien et al. | 606/41 |
| 2004/0039249 A1* | 2/2004 | Shiro et al. | 600/101 |
| 2004/0064139 A1* | 4/2004 | Yossepowitch | 606/46 |
| 2004/0172018 A1* | 9/2004 | Okada | 606/46 |

FOREIGN PATENT DOCUMENTS

| | | |
|---|---|---|
| JP | 7-008503 | 1/1995 |
| JP | 8-299355 | 11/1996 |
| JP | 2002-153484 | 5/2002 |
| WO | 01/58360 | 8/2001 |

OTHER PUBLICATIONS

English Language Abstract of JP 2002-153484.
English Language Abstract of JP 6-292685.
English Language Abstract of JP 8-299355.
U.S. Appl. No. 11/085,512 to Ouchi, filed Mar. 22, 2005.

* cited by examiner

HIGH FREQUENCY TREATMENT INSTRUMENT FOR ENDOSCOPE

TITLE OF THE INVENTION

High Frequency Treatment Instrument For Endoscope

BACKGROUND OF THE INVENTION

The present invention relates to a high frequency treatment instrument to be inserted into an instrument-inserting channel of an endoscope for endoscopic mucosal resection (EMR).

There are various types of high frequency treatment instruments used for EMR. Japanese Patent Provisional Publication No. HEI 7-8503 (hereafter, referred to as a document 1) discloses a high frequency treatment instrument, which includes an insulative flexible sheath and a hook-like electrode located at a tip of the flexible sheath. The hook-like electrode includes a rod-like part elongated frontward from the tip of the flexible sheath, and a hook-like part projected in a lateral direction from a tip of the rod-like part.

The treatment instrument disclosed in the document 1 allows an operator to perform a endscopic treatment easily. However, the treatment instrument has a drawback that the hook-like electrode may accidentally damage an instrument-inserting channel of an endoscope or mucous membranes of a body cavity.

Japanese Patent Provisional Publication No. 2002-153484 (hereafter, referred to as a document 2) discloses a different type of treatment instrument. The treatment instrument disclosed in the document 2 is configured such that the hook-like electrode is retractable with respect to a tip of a flexible sheath. By this structure, the above mentioned drawback of the conventional treatment instrument can be solved.

SUMMARY OF THE INVENTION

However, since the treatment instrument of the document 2 is configured such that the rod-like part of the hook-like electrode is situated along an axial line of the flexible sheath, an adequate length of a hook part is not secured.

The present invention is advantageous in that it provides a high frequency treatment instrument configured to secure an adequate length of a hook part.

According to an aspect of the invention, there is provided a high frequency treatment instrument for an endoscope, which is provided with an insulative flexible sheath, an operation wire inserted in the flexible sheath so as to be movable along an axial direction of the operation wire in the flexible sheath, and a hook-like electrode attached to a tip of the operation wire. The hook-like electrode includes a rod-like part which is elongated in parallel with the axial direction along a line shifted from an axis line of the operation wire, and a hook part elongated from the rod-like part to cross the axis line of the operation wire.

With this structure, an adequate length of the hook part is secured.

Optionally, the hook part may project from a tip of the rod-like part in a lateral direction.

Still optionally, the hook-like electrode may include a wide part expanded at a base portion of the rod-like part in a direction in which the hook part projects from the rod-like part.

Still optionally, at least a tip portion of the flexible sheath may be formed of a flexible tube. In this case, the wide part of the hook-like electrode is retracted into the flexible tube to press and broaden the flexible tube from an inside of the flexible tube when the operation wire is moved backward.

Still optionally, the high frequency treatment instrument may include an operation unit attached to a base of the flexible sheath. The operation unit may have a movable hook connected to a base of the operation wire to move back and forth the operation wire in the axial direction.

Still optionally, the operation wire may be rotatable about the axis line thereof relative to the flexible sheath.

Still optionally, the high frequency treatment instrument may include a holding ring attached to a base portion of the flexible sheath so that the operation wire is rotated about the axis line while holding the holding ring.

Still optionally, the axis line of the operation wire may coincide with a center axis of the wide part.

Still optionally, the hook-like electrode may include a slanting part elongated from a tip of the rod-like part in a slanting direction to cross the axis line of the operation wire. In this case, the hook part may be elongated straight from a tip of the slanting part and then is bent in a lateral direction to cross the axis line of the operation wire.

Still optionally, wherein the rod-like part, the slanting part and the hook part may be in one plane.

In a particular case, the hook-like electrode may be formed of a flat steel plate.

In a particular case, bumps and dips may be formed at a rear edge of the slanting part.

In a particular case, a front edge of the hook part is formed to have a wavy shape.

BRIEF DESCRIPTION OF THE ACCOMPANYING DRAWINGS

DETAILED DESCRIPTION OF THE EMBODIMENTS

Hereinafter, embodiments according to the invention are described with reference to the accompanying drawings.

First Embodiment

Figure 2:
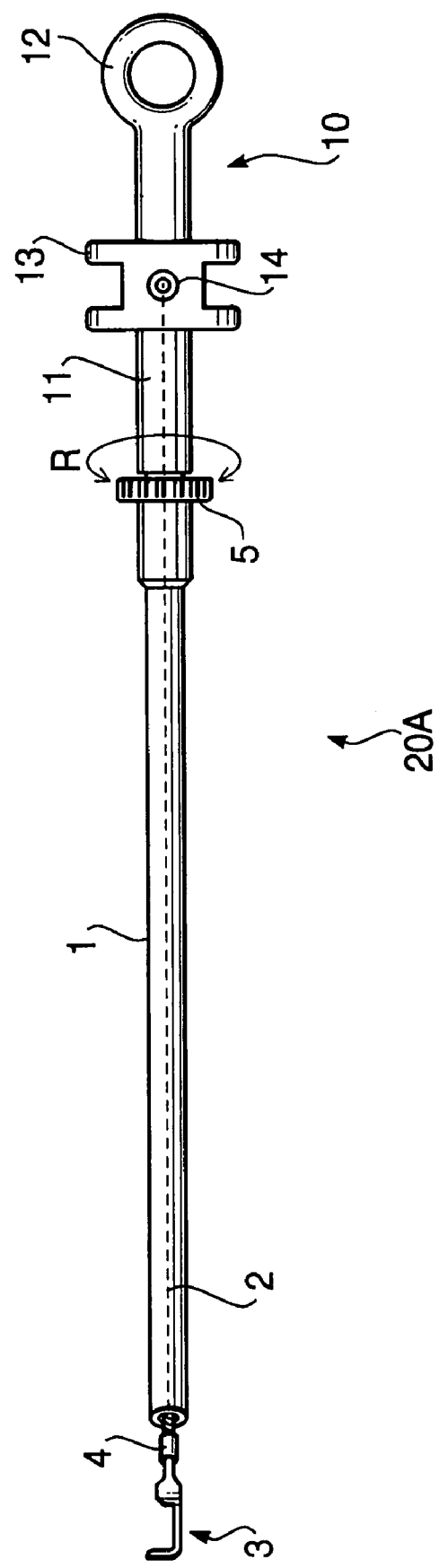
FIG. 2 is a general view of the high frequency treatment instrument according to the first embodiment.

FIG. 2 is a general view of a high frequency treatment instrument 20A for endoscopes according to a first embodiment of the invention. The treatment instrument 20A includes a flexible sheath 1 formed of an insulative flexible tube such as a tetrafluoroethylene resin tube. A conductive operation wire 2 is disposed in the inside of the flexible sheath 1 along the length of the flexible sheath 1 so that the operation wire 2 is movable along an axial direction of the operation wire 2. The flexible sheath 1 may be configured such that at least a tip portion thereof is formed of a flexible tube.

A conductive hook-like electrode 3 (for example, formed of a stainless steel plate) is connected to a tip of the operation wire 2 via a connection pipe 4 (for example, formed of a stainless steel pipe) so that the hook-like electrode 3 is retractable with respect to the tip of the flexible sheath 1. That is, the hook-like electrode 3 moves forward or backward with respect to the tip of the flexible sheath 1.

At a base part of the flexible sheath 1, an operation unit 10 is connected. The operation unit 10 is used to move the operation wire 2 along the axial direction of the operation wire 2 in the flexible sheath 1. The operation unit 10 includes an operation main body 11, a fixed hook 12 formed at a base end of the operation main body 11, and a movable hook 13 slidably attached to the operation main body 11. A base of the operation wire 2, which is pulled straight in the flexible sheath 1 toward the operation unit 10, is connected to the movable hook 13.

In this structure, the operation wire 2 moves along the axial direction in the flexible sheath 1 by operating the movable hook 13 to move forward or backward along the axial direction. As a result, the hook-like electrode 3 is protruded from or retracted into the tip portion of the flexible sheath 1.

A connector 14 to which a high-frequency power source cable can be connected is located on the movable hook 13 of the operation unit 10, so that a high-frequency current can be supplied to the hook-like electrode 3 via the operation wire 2.

The base part of the flexible sheath 1 is attached to the operation main body 11 such that the flexible sheath 1 is fixed in the axial direction thereof and is rotatable about the axis thereof. At the base of the flexible sheath 1, a holding ring 5 is fixed.

By operating the operation unit 10 to rotate about the axis as illustrated by an arrow R in FIG. 2 while holding the holding ring 5, the operation wire 2 rotates about the axis in the flexible sheath 1 and the hook-like electrode 3 rotates about the axis. Therefore, an operator can set the rotational direction of the hook-like electrode at a desirable direction by operating the operation unit 10.

Figure 1:
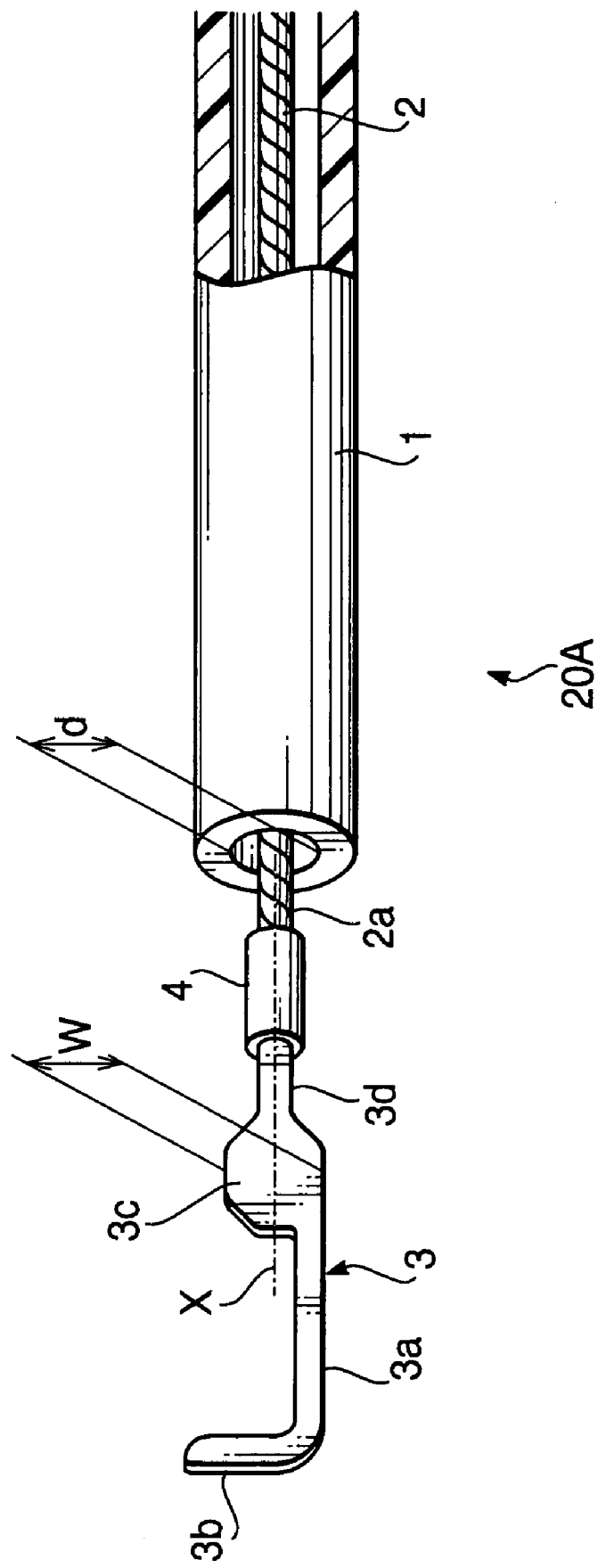
FIG. 1 is a perspective view of a tip portion of a high frequency treatment instrument according to a first embodiment of the invention.

FIG. 1 shows a tip portion of the treatment instrument 20A. As shown in FIG. 1, the hook-like electrode 3 has a rod-like part 3a which is elongated in parallel with an axis line of the tip portion of the flexible sheath 1 and is shifted from an axis line of the operation wire 2, and a hook part 3b projecting in a lateral direction from a tip of the rod-like part 3a.

Although, in this embodiment, the hook part 3b is formed in such a manner that the hook part 3b bends approximately 90 degrees with respect to the rod-like part 3a, the hook part 3b may be formed to bend at an acute angle or obtuse angle with respect to the rod-like part 3b. The hook part 3b may be formed to have a round shape.

On a base side of the hook-like electrode 3, a wide part 3c is formed. The wide part 3c is expanded from a base of the rod-like part 3a in a direction in which the hook part 3b projects from the tip of the rod-like part 3a. An extension of a center line X of the wide part 3c coincides with a tip portion 2a of the operation wire 2.

As shown in FIG. 1, corners of the wide part 3c are cut away such that an edge of the wide part 3c bends at 45 degrees at each corner portion. Alternatively, each corner part may be cut away so that the edge has a round shape at each corner portion. A slender part 3d is formed at the base of the wide part 3c so as to be connected to the connection pipe 4.

The wide part 3c is configured to have a width W larger than an internal diameter d of the flexible sheath 1 to some extent (i.e. W>d). For example, a difference (W−d) may be within 0.1 through 0.3 mm.

Figure 3:
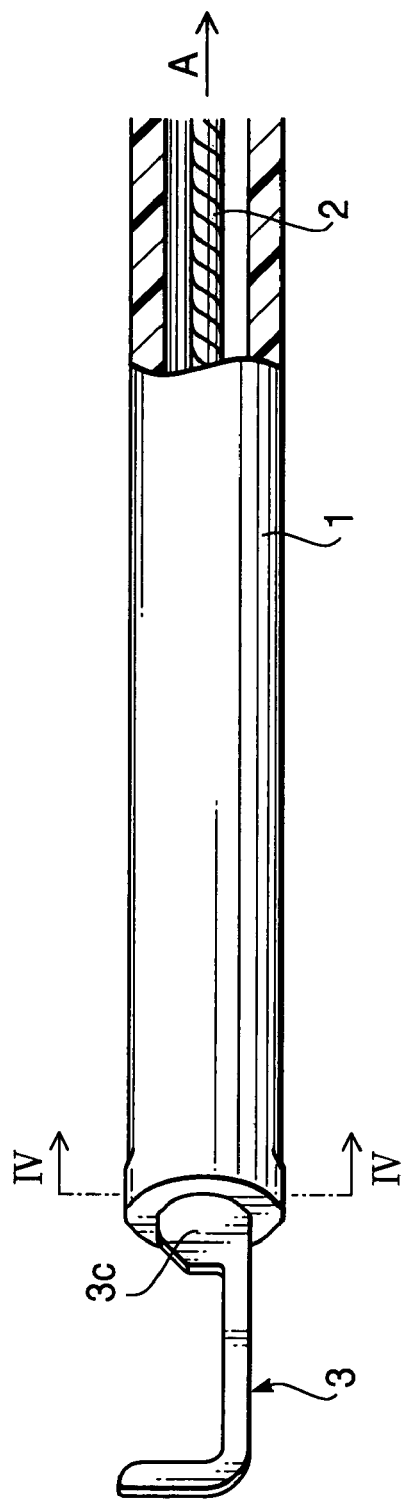
FIG. 3 is a perspective view of the high frequency treatment instrument illustrating a situation where a wide part of a hook-like electrode is retracted into a tip of a flexible sheath.
Figure 4:
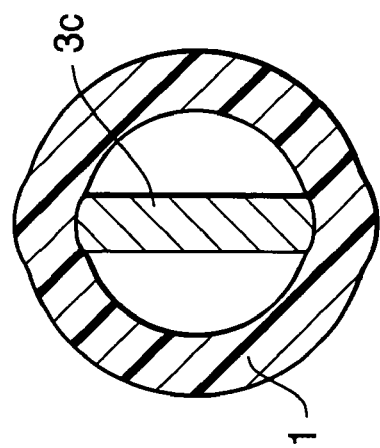
FIG. 4 is a cross-sectional view of the high frequency treatment instrument along a line IV-IV of FIG. 3.

Therefore, if the operation wire 2 is pulled in a direction A shown in FIG. 3 by operating the operation unit 10 to retract the wide part 3c into the inside of the tip portion of the flexible sheath 1, the wide part 3c fits into the inside of the tip portion (i.e. a flexible tube part) of the flexible sheath 1 in such a manner that the edge of the wide part 3c presses and broadens the inner surface of the flexible sheath 1 as illustrated in FIG. 4 which is a cross-sectional view the treatment instrument 20A along a line IV-IV of FIG. 3. In this state, the hook-like electrode 3 is securely held by the inner surface of the flexible sheath 1.

Figure 5:
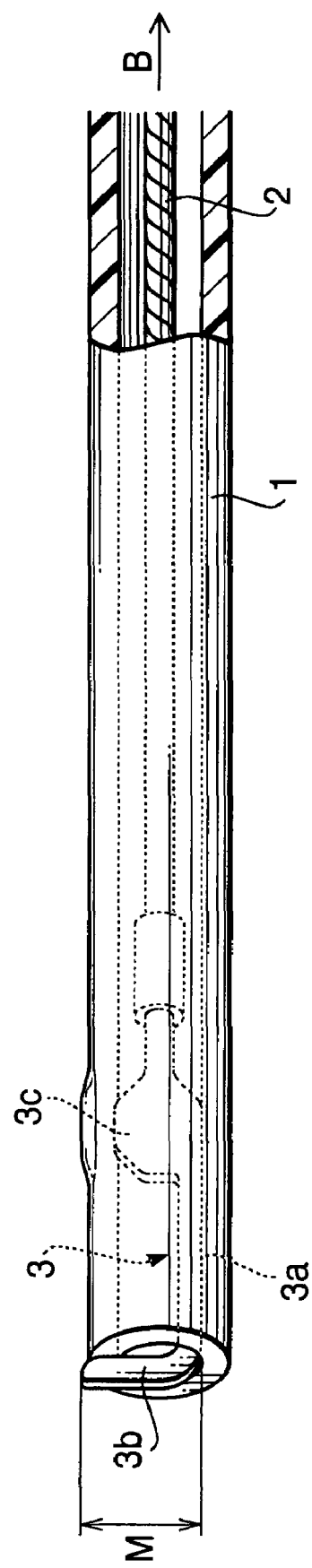
FIG. 5 is a perspective view of the high frequency treatment instrument illustrating a situation where the hook-like electrode is fully retracted into the flexible sheath.

As shown in FIG. 5, if the operation wire 2 is pulled at the maximum in a direction B by operating the operation unit 10, the hook-like electrode 3 moves backward in the tip portion of the flexible sheath 1 until the hook part 3c contacts the tip of the flexible sheath 1. In this stage of FIG. 5, almost no portion of the hook part 3b protrudes from an outer circumferential surface of the flexible sheath 1. It is noted that the tip may slightly project from the outer circumferential surface of the flexible sheath 1 if the projected amount from the outer circumferential surface is within an acceptable degree that the projected part does not damage an instrument-inserting channel of an endoscope.

Therefore, according to the embodiment, a size determined by subtracting a wall thickness of the flexible sheath 1 from the outside diameter of the flexible sheath 1 is secured as a length M of the hook part 3*b*.

Figure 6:
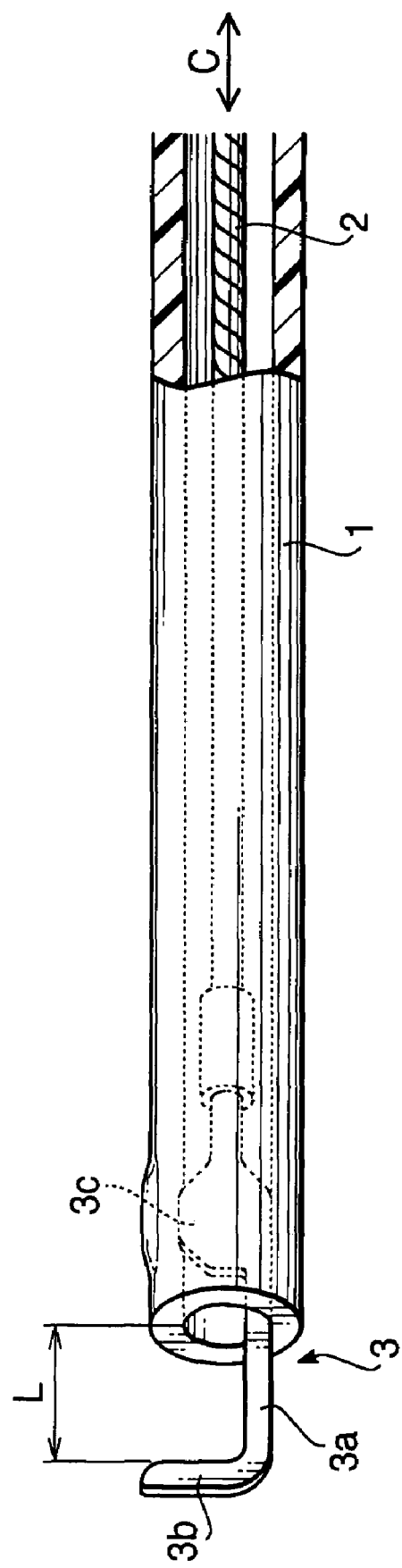
FIG. 6 is a perspective view of the high frequency treatment instrument illustrating a situation where about half part of the hook-like electrode is retracted into the flexible sheath.

By operating the movable hook 13 to move the operation wire 2 in a direction C shown in FIG. 6, the hook-like electrode 3 can be fixed at desired positions. For example, the hook-like electrode 3 can be fixed at a position at which the hook-like electrode 3 is projected by a desirable length L from the tip of the flexible sheath 1.

In this state, the hook-like electrode 3 is fixed in the tip portion of the flexible sheath 1 by a reaction force applied to the edge of the wide part 3*c* by the flexible sheath 1. Therefore, even if an external force smaller than a fixing force of the flexible sheath 1 acts on the hook-like electrode 3, the hook-like electrode 3 does not move with respect to the tip of the flexible sheath 1.

Therefore, occurrence of an undesirable phenomenon that the hook-like electrode 3 rotates about the axis line of the flexible sheath 1 when the hook-like electrode 3 is pressed against a mucous membrane is prevented. It becomes possible to perform an endoscopic treatment (e.g. mucosa incision) as desired by an operator. Also, since the adequate length M of the hook part 3*b* is secured, excellent cutting performance is attained.

Figure 7:
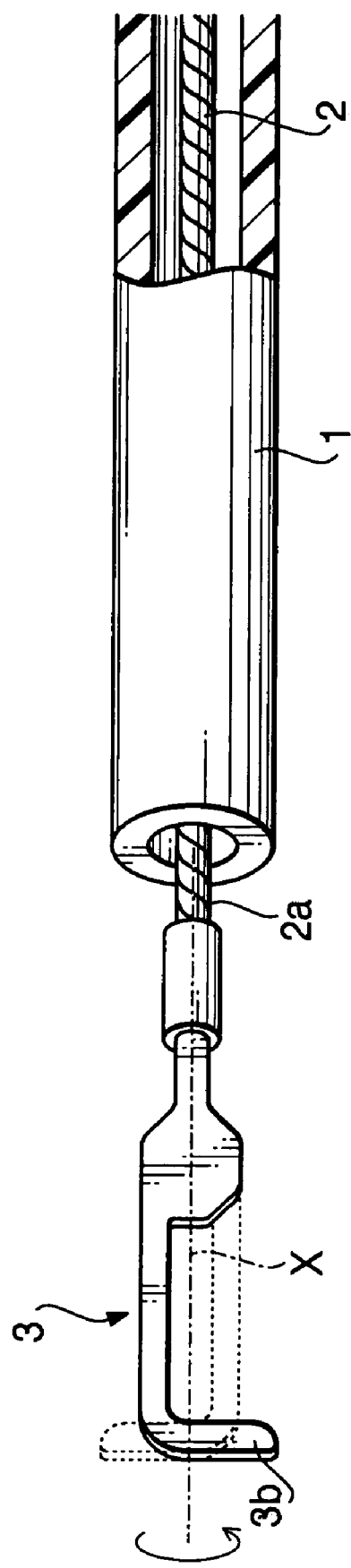
FIG. 7 is a perspective view of the high frequency treatment instrument illustrating a situation where the hook-like electrode is rotated.

By operating the operation unit 10 to rotate the operation wire 2 about the axis line of the flexible sheath 1 while the entire part of the hook-like electrode 3 is projected from the tip of the flexible sheath 1, the rotational direction of the hook-like electrode 3*b* can be set at a desirable direction as indicated by an arrow in FIG. 7.

Figure 8:
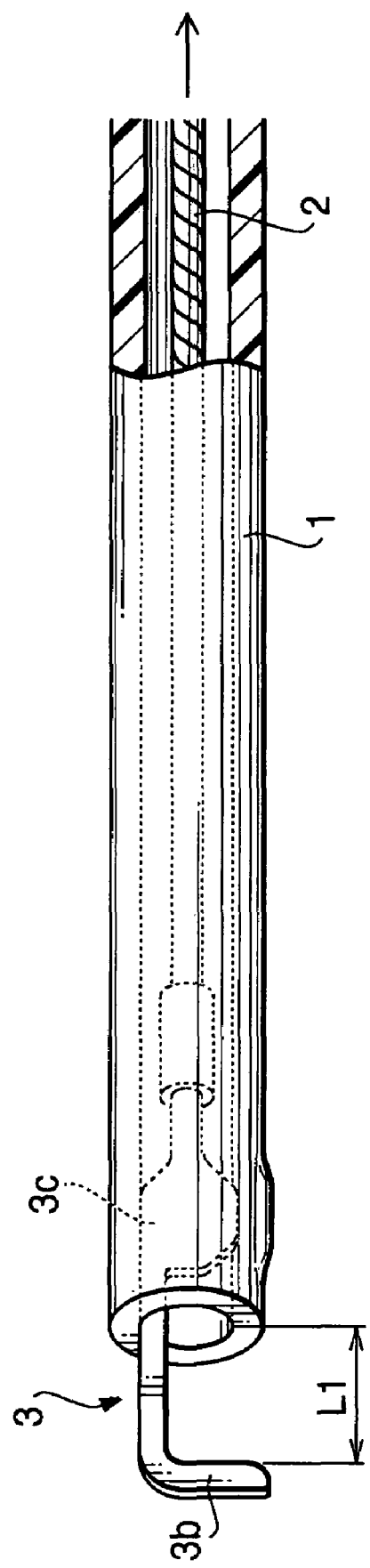
FIG. 8 is a perspective view of the high frequency treatment instrument illustrating a situation where about half part of the hook-like electrode is retracted into the flexible sheath after the hook-like electrode is rotated.

As shown in FIG. 8, by pulling the operation wire 2 to retract the wide part 3*c* of the hook-like electrode 3 into the flexible sheath 1 after the direction of the hook part 3*b* is adjusted at a desirable direction, the endoscopic treatment can be performed in an appropriate condition where the projected length of the hook part 3*b* from the tip of the flexible sheath 1 is set at a desirable length L1 and the direction of the hook part 3*b* is set at a desirable direction.

Second Embodiment

Figure 9:
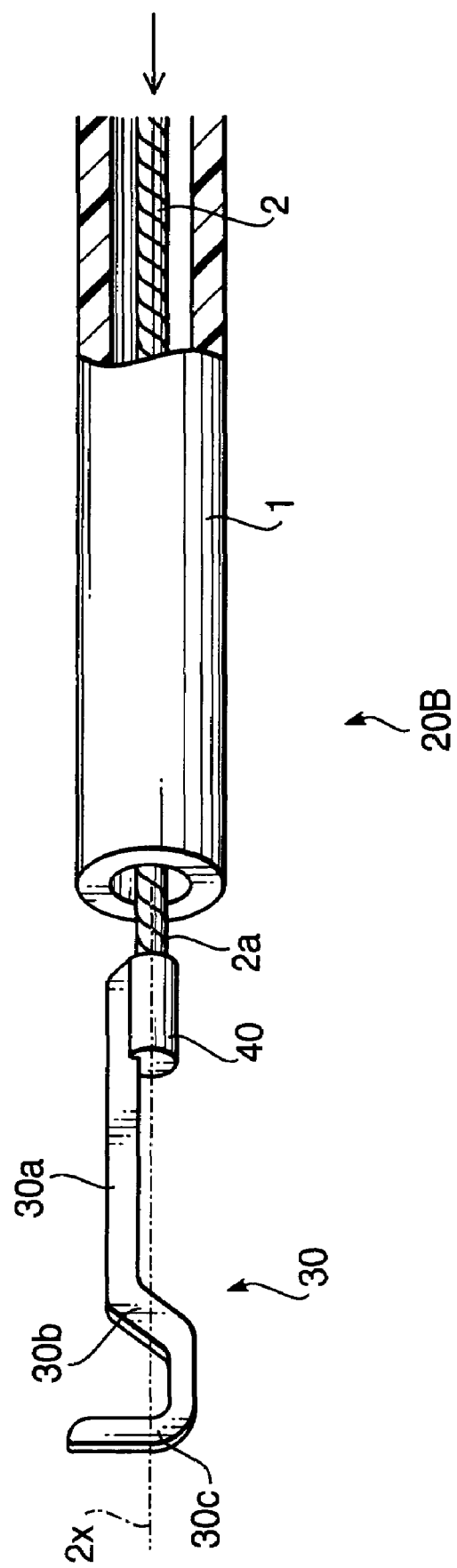
FIG. 9 is an enlarged view of a tip portion of a high frequency treatment instrument according to a second embodiment of the invention.
Figure 10:
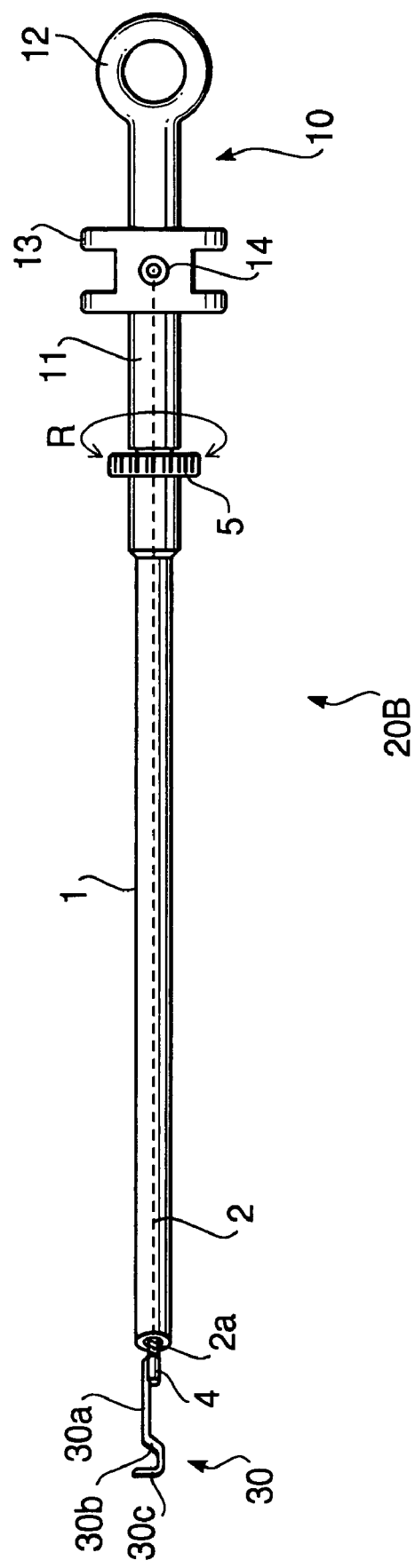
FIG. 10 is a general view of the high frequency treatment instrument according to the second embodiment.

FIG. 9 is an enlarged view of a tip portion of a high frequency treatment instrument 20B for endoscopes according to a second embodiment of the invention. FIG. 10 is a general view of the treatment instrument 20B according to the second embodiment. In FIGS. 9 and 10 (and in the other drawings of the second embodiment), to elements which are similar to those of the first embodiment, the same reference numbers are assigned, and the detailed description thereof will not be repeated.

The treatment instrument 20B includes a hook-like electrode 30 connected to the tip portion 2*a* of the operation wire 2. Similarly to the first embodiment, the hook-like electrode 30 moves frontward or backward by operating the operation unit 10 to move the operation wire 2 in the axial direction of the flexible sheath 1.

As shown in FIG. 9, the hook-like electrode 30 includes a rod-like part 30*a* elongated in a forward direction from the tip of the operation wire 2 along a line which is shifted from an extension 2*x* of an axis line of the operation wire 2 and is parallel with the extension 2*x*. The hook-like electrode 30 further includes a slanting part 30*b* elongated from a tip of the rod-like part 30*a* in a slanting direction to cross the extension 2*x* of the operation wire 2. The hook-like electrode 30 further includes a front-end hook 30*c* formed such that the front-end hook 30 is elongated straight from a tip of the slanting part 30*b* and then is bent in a lateral direction to cross the extension 2*x*.

The hook-like electrode 30 may be produced, for example, by subjecting a stainless steel plate having a thickness of within 0.2 mm through 0.5 mm to a cutting process or a stamping process. The rod-like part 30*a*, the slanting part 30*b* and the front-end hook 30*c* are in one plane. If the thickness of the hook-like electrode 30 is smaller than the range of 0.2 mm through 0.5 mm, cutting performance of the hook-like electrode 30 may become too strong. If the thickness of the hook-like electrode 30 is larger than the range of 0.2 mm through 0.5 mm, heat-caused damage to a peripheral portion of a cutting target of mucosa may become heavy.

A base of the rod-like part 30*a* is fitted into a straight groove (not shown) formed in a connecting member 40 and is fixed to the connecting member 40, for example, by brazing. Also, the tip portion 2*a* of the operation wire 2 is inserted into a hole formed in the connecting member 40 and is fixed to the connecting member 40, for example, by brazing.

Figure 11:
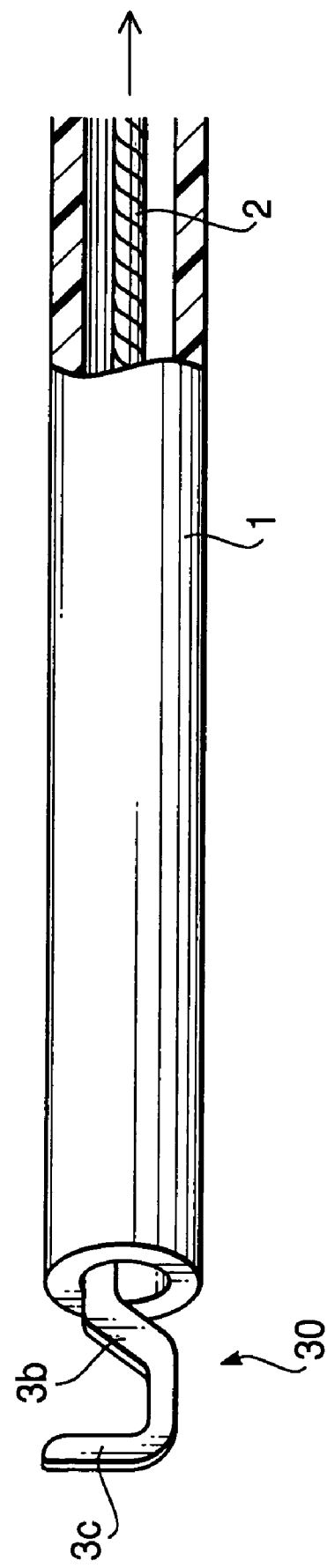
FIG. 11 is a perspective view of the high frequency treatment instrument according to the second embodiment illustrating a situation where a hook-like electrode is fully retracted into a tip of a flexible sheath.

According to the above mentioned structure, as shown in FIG. 9, the hook-like electrode 3 moves forward from the tip of the flexible sheath 1 by operating the operation unit 10 to press forward the operation wire 2. As shown in FIG. 11, the hook-like electrode 30 is retracted into the tip portion of the flexible sheath 1 by operating the operation unit 10 to pull backward the operation wire 2.

The treatment member 20B configured as above is used for three types of treatments including a marking treatment, a mucosa cutting treatment and an exfoliation treatment.

Figure 12:
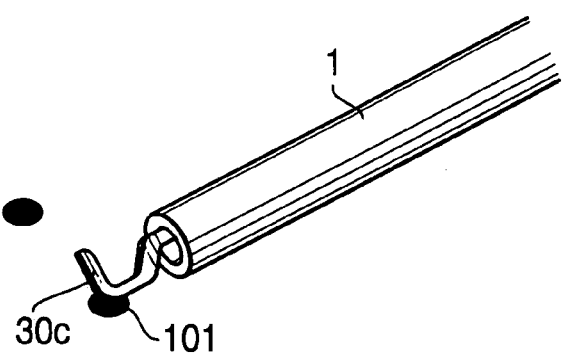
FIG. 12 shows a situation where the hook-like electrode according to the second embodiment is used for a marking treatment.

FIG. 12 shows a situation where the hook-like electrode 30 is used for the marking treatment for forming markings 101 around a target part (affected area) on mucosa. The markings 101 may be formed by supplying a high frequency current to the hook-like electrode 30 for a short time period while a curved part of the hook-like electrode 30 contacts a point (a position of each marking 101) in the peripheral portion of the target part. Each marking 101 is formed as a punctiform burn injury. By using the curved part of the hook-like electrode 30 for the marking treatment, the possibility of accidentally forming a hole in the mucosa decreases in comparison with a case where the tip of the front-end hook 30*c* is used for the marking treatment.

Figure 13:
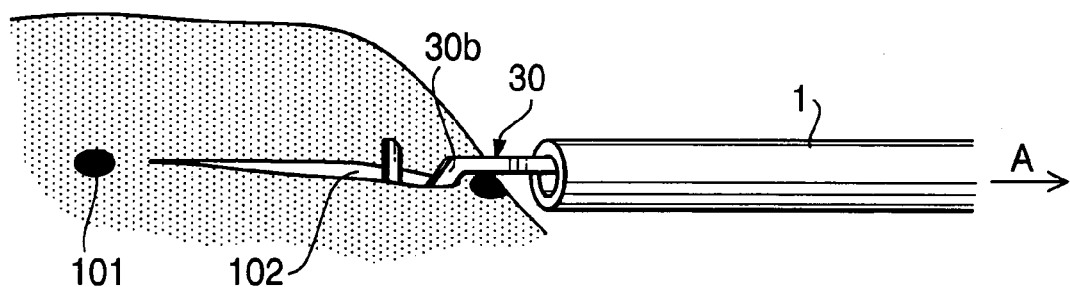
FIG. 13 shows a situation where the hook-like electrode according to the second embodiment is used for a mucosa cutting treatment.

After the marking treatment is finished, the affected area of the mucosa is upraised by infusing a submucous part under the affected area with physiological saline as a preparation to the mucosa cutting treatment. In the mucosa cutting treatment, a rear edge of the slanting part 30*b* of the hook-like electrode 30 is used to cut the mucosa (as indicated by a reference numerical 102 in FIG. 13) in such a manner that the rear edge of the slanting part 30*b* is pressed against the mucosa surface while supplying the high frequency current to the hook-like electrode 30 and moving the hook-like electrode 30 backward (in a direction indicated by an arrow A in FIG. 13) along the markings 101.

Figure 14:
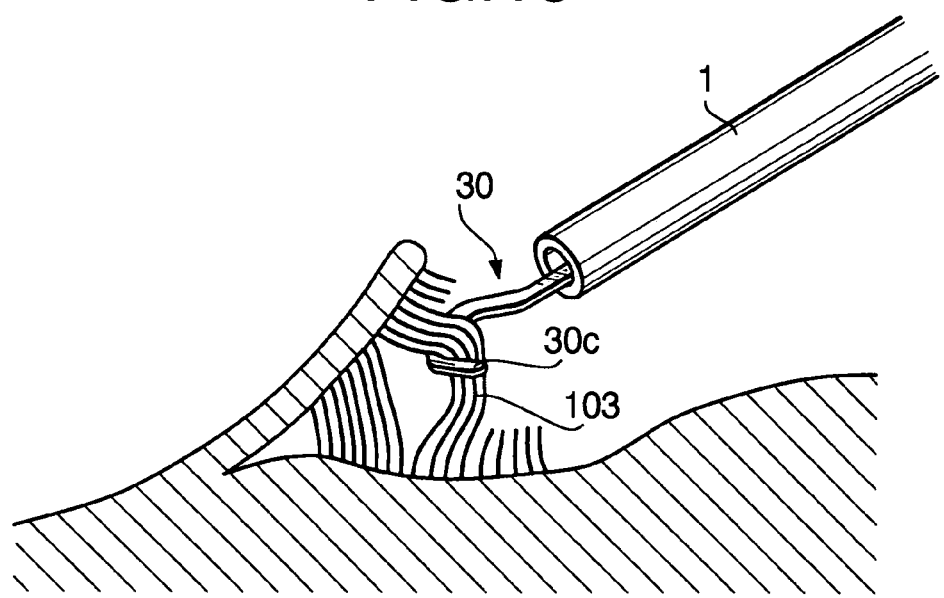
FIG. 14 shows a situation where the hook-like electrode according to the second embodiment is used for an exfoliation treatment.

Next, the exfoliation treatment is performed by hooking the front-end hook 30*c* to muscular tissue 103 between the mucosa surface and a muscle layer and then supplying a high frequency current to the hook-like electrode 30 as shown in FIG. 14. By such an exfoliation treatment, the muscular tissue 103 is cut and the affected area of the mucosa is detached effectively.

As described above, three treatments including the marking treatment, the mucosa cutting treatment and the exfoliation treatment are continuously performed without replacing the treatment instrument 20B with another one.

Similarly to the first embodiment, an adequate length of the front-end hook 30c is secured since the rod-like part 30a is shifted from the axis line of the operation wire 2.

Although the present invention has been described in considerable detail with reference to certain preferred embodiments thereof, other embodiments are possible.

Figure 15:
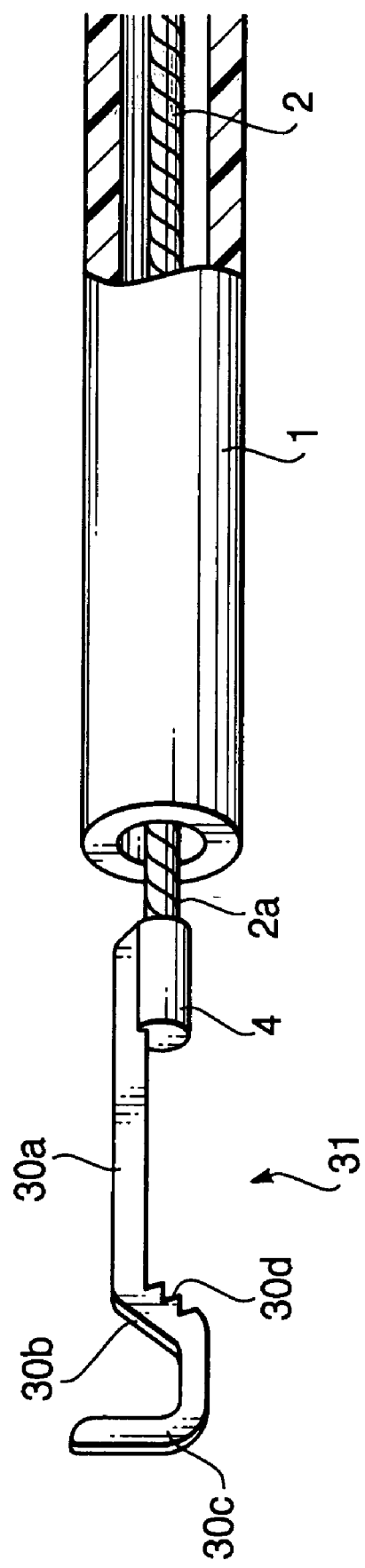
FIG. 15 is an enlarged view of a tip portion of a high frequency treatment instrument as a first variation of the high frequency treatment instrument of the second embodiment.

For example, bumps and dips may be formed at a rear edge of the slanting part 30b of the hook-like electrode 30. FIG. 15 shows such a hook-like electrode 31. The hook-like electrode 31 has the slanting part 30b provided with bumps and dips 30d at its rear edge. If the hook-like electrode 31 is used for the mucosa cutting treatment, the bumps and dips 30d of the slanting part 30b functions as an anti slip member for keeping the hook-like electrode 31 from slipping from mucosa and keeping the slanting part 30b from being raised form the mucosa. The slip resistance property produced by the bumps and dips 30d may be enhanced by sharpening corners of the bumps and dips 30d.

Figure 16:
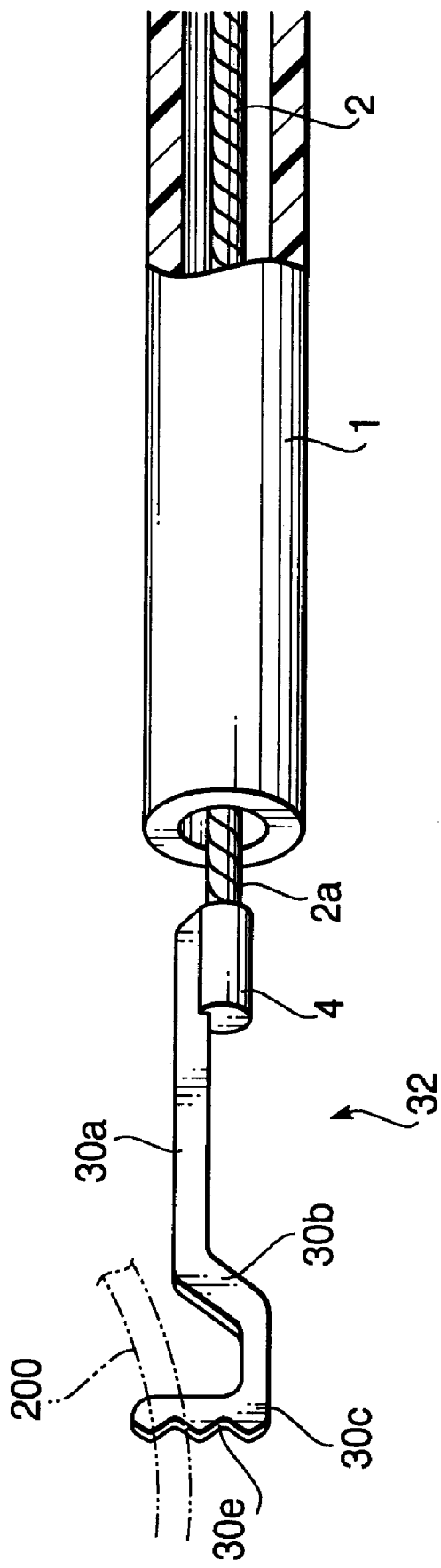
FIG. 16 is an enlarged view of a tip portion of a high frequency treatment instrument as a second variation of the high frequency treatment instrument of the second embodiment.

Wavy part 30e may be formed at the front edge of the front-end hook 30c. FIG. 16 shows such a hook-like electrode 32. If the hook-like electrode 32 is used for the exfoliation treatment, bleeding from a blood vessel 200 can be quickly stopped by pressing the wavy part 30e against the blood vessel 200 and then supplying a high frequency current to the hook-like electrode 32.

Figure 17:
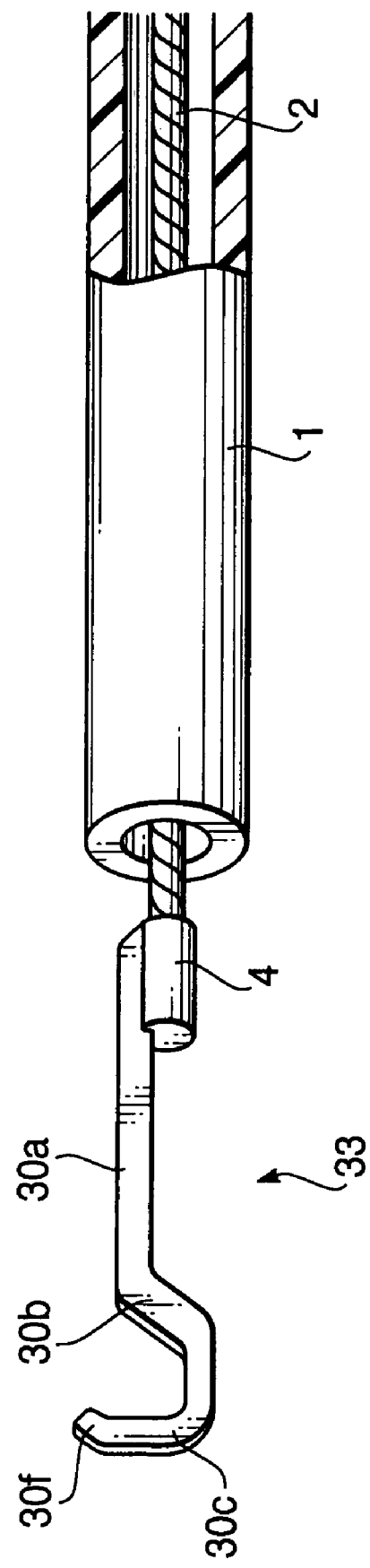
FIG. 17 is an enlarged view of a tip portion of a high frequency treatment instrument as a third variation of the high frequency treatment instrument of the second embodiment.
Figure 18:
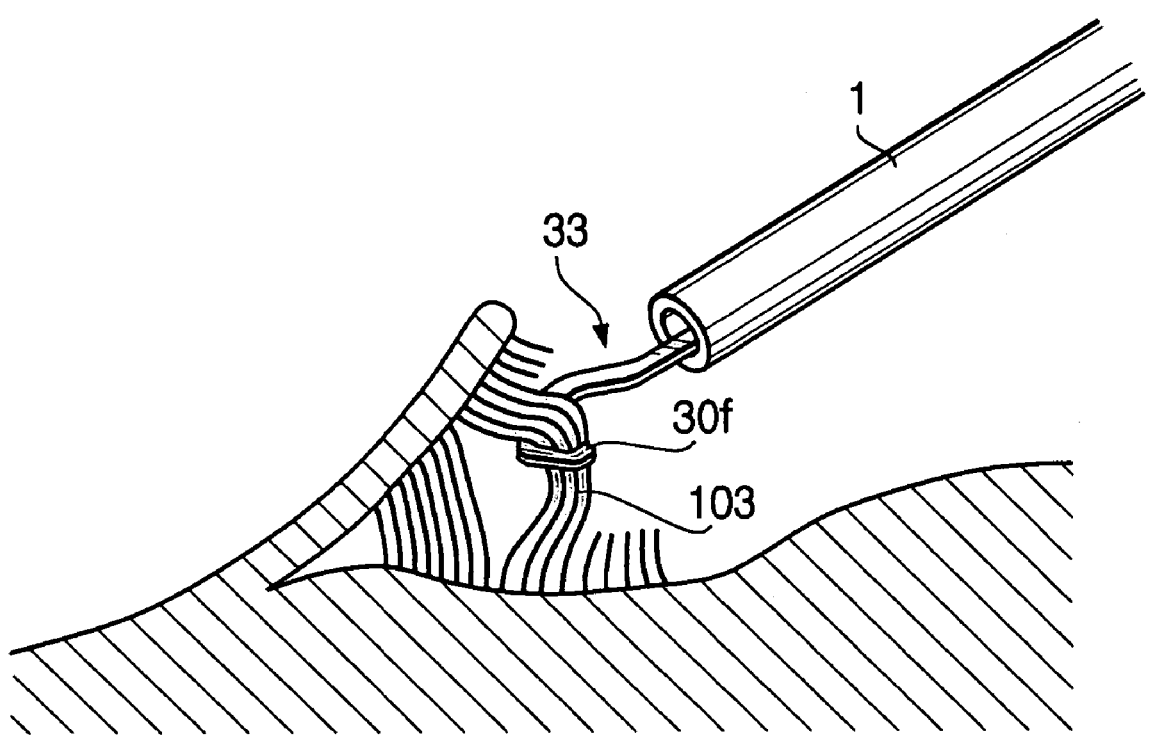
FIG. 18 shows a situation where the hook-like electrode of the third variation shown in FIG. 17 is used for an exfoliation treatment.

A returning part 30f may be formed at the tip of the front-end hook 30c. FIG. 17 shows such a hook-like electrode 33. The returning part 30f is bent backward from the tip of the front end hook 30c. As shown in FIG. 18, if the hook-like electrode 33 is used for the exfoliation treatment, the returning part 30f securely holds the muscular tissue 103 and therefore the exfoliation treatment can be performed more easily and reliably.

The present disclosure relates to the subject matters contained in Japanese Patent Applications Nos. 2004-085847, filed on Mar. 24, 2004, and 2004-151268, filed on May 21, 2004, which are expressly incorporated herein by reference in their entireties.

What is claimed is:

1. A high frequency treatment instrument for an endoscope, comprising:
   an insulative flexible sheath;
   an operation wire inserted in the flexible sheath so as to be movable along an axial direction of the operation wire in the flexible sheath; and
   a hook-like electrode attached to a tip of the operation wire, wherein the hook-like electrode includes:
   a rod-like part that extends parallel to the axial direction of the operation wire and is spaced from an axis of the operation wire; and
   a slanting part that extends from a tip of the rod-like part in a slanting direction to cross the axis of the operation wire; and
   a hook part that extends from the slanting part in a direction to cross the axis of the operation wire; and
   wherein the hook part extends straight from a tip of the slanting part and then bends in a lateral direction to cross the axis of the operation wire, and the rod-like part, the slanting part and the hook part lie in one plane; and
   wherein the hook-like electrode is retractable into the flexible sheath to an extent that the entire rod-like part is within the flexible sheath.

2. The high frequency treatment instrument according to claim 1, wherein the hook part projects from a tip of the rod-like part in a direction transverse to the axial direction.

3. The high frequency treatment instrument according to claim 2, wherein the hook-like electrode, at a base portion of the rod-like part, includes a wider part that is wider than another part of the rod-like part, in a direction in which the hook part projects from the rod-like part.

4. The high frequency treatment instrument according to claim 3, wherein the axis of the operation wire coincides with a center axis of the wider part.

5. The high frequency treatment instrument according to claim 3, wherein:
   at least a tip portion of the flexible sheath comprises a flexible tube; and
   the wider part of the hook-like electrode is retracted into the flexible tube to press and expand the flexible tube from an inside of the flexible tube when the operation wire is moved in a direction so as to retract the electrode.

6. The high frequency treatment instrument according to claim 5, the wider part being integrally formed with the hook-like electrode and configured to expand an outer periphery of the flexible sheath.

7. The high frequency treatment instrument according to claim 1, further comprising an operation unit attached to a base of the flexible sheath,
   wherein the operation unit has a movable hook connected to a base of the operation wire to move the operation wire back and forth in the axial direction.

8. The high frequency treatment instrument according to claim 1, wherein the operation wire is rotatable about the axis of the operation wire with respect to the flexible sheath.

9. The high frequency treatment instrument according to claim 8, further comprising a holding ring attached to a base portion of the flexible sheath so that the operation wire is rotated about the axis while holding the holding ring.

10. The high frequency treatment instrument according to claim 1, wherein the hook-like electrode comprises a flat steel plate.

11. The high frequency treatment instrument according to claim 1, wherein bumps and dips are provided at a rear edge of the slanting part.

12. The high frequency treatment instrument according to claim 1, wherein a front edge of the hook part is configured to have a wavy shape.

13. The high frequency treatment instrument according to claim 1, the hook-like electrode being configured to contact the flexible sheath when the hook-like electrode is retracted into the flexible sheath.

14. The high frequency treatment instrument according to claim 1, wherein, when the hook-like electrode is retracted, the hook part remains outside the flexible sheath.

15. The high frequency treatment instrument according to claim 1, wherein the hook part extends across substantially an entire inner diameter of the flexible sheath.

16. The high frequency treatment instrument according to claim 1, the hook part being configured to contact an end face of the flexible sheath when the rod like part is within the flexible sheath.

17. The high frequency treatment instrument according to claim 1, at least one edge surface of the hook-like electrode comprises an anti-slip surface.

18. The high frequency treatment instrument according to claim 1, at least one edge surface of the hook-like electrode comprises a cutting surface.

* * * * *

(12) EX PARTE REEXAMINATION CERTIFICATE (7725th)
United States Patent
Ouchi

(10) Number: US 7,402,162 C1
(45) Certificate Issued: Sep. 7, 2010

(54) HIGH FREQUENCY TREATMENT INSTRUMENT FOR ENDOSCOPE

(75) Inventor: Teruo Ouchi, Saitama (JP)

(73) Assignee: Hoya Corporation, Shinjuku-Ku, Tokyo (JP)

Reexamination Request:
No. 90/009,420, Feb. 27, 2009

Reexamination Certificate for:
Patent No.: 7,402,162
Issued: Jul. 22, 2008
Appl. No.: 11/086,436
Filed: Mar. 23, 2005

(30) Foreign Application Priority Data

Mar. 24, 2004 (JP) ........................ 2004-085847
May 21, 2004 (JP) ........................ 2004-151268

(51) Int. Cl.
*A61B 18/18* (2006.01)

(52) U.S. Cl. .................. 606/45; 606/1; 606/46
(58) Field of Classification Search .................. None
See application file for complete search history.

(56) References Cited

U.S. PATENT DOCUMENTS

| | | | |
|---|---|---|---|
| 4,311,143 A | 1/1982 | Komiya |
| 4,492,832 A | 1/1985 | Taylor |
| 4,733,662 A | 3/1988 | DeSatnick et al. |
| 5,057,107 A | 10/1991 | Parins et al. |
| 5,261,906 A | 11/1993 | Pennino et al. |
| 5,401,274 A | 3/1995 | Kusunoki |
| 5,460,629 A | 10/1995 | Shlain et al. |
| 5,480,398 A | 1/1996 | Eggers |
| 5,628,760 A | 5/1997 | Knoepfler |
| 5,891,141 A | 4/1999 | Rydell |
| 5,936,536 A | 8/1999 | Morris |
| 5,938,661 A | 8/1999 | Hahnen |
| 6,007,514 A | 12/1999 | Nita |
| 6,059,782 A | 5/2000 | Novak et al. |
| 6,190,384 B1 | 2/2001 | Ouchi |
| 6,428,503 B1 | 8/2002 | Kierce |
| 6,478,794 B1 | 11/2002 | Trapp et al. |
| 6,730,081 B1 | 5/2004 | Desai |
| 6,808,525 B2 | 10/2004 | Latterell et al. |
| 7,060,056 B2 | 6/2006 | Palasis et al. |
| 2003/0040744 A1 | 2/2003 | Letterell et al. |
| 2003/0130655 A1 | 7/2003 | Woloszko et al. |
| 2003/0163123 A1 | 8/2003 | Goble et al. |
| 2004/0019350 A1 | 1/2004 | O'Brien et al. |
| 2004/0039249 A1 | 2/2004 | Shiro et al. |
| 2004/0064139 A1 | 4/2004 | Yossepowitch |
| 2004/0172018 A1 | 9/2004 | Okada |
| 2005/0222567 A1 | 10/2005 | Ouchi |

FOREIGN PATENT DOCUMENTS

| | | |
|---|---|---|
| DE | 3707820 | 9/1987 |
| DE | 20008639 | 11/2000 |
| DE | 10122731 | 11/2002 |
| JP | 5-293115 | 11/1993 |
| JP | 5-093411 | 12/1993 |
| JP | 6-292685 | 10/1994 |
| JP | 7-008503 | 1/1995 |
| JP | 8-299355 | 11/1996 |
| JP | 2002-153484 | 5/2002 |
| WO | 01/58360 | 8/2001 |

OTHER PUBLICATIONS

English language Abstract of JP 6-292685.
English language Abstract of JP 7-008503.

(Continued)

*Primary Examiner*—Catherine S. Williams

(57) ABSTRACT

A high frequency treatment instrument for an endoscope is provided. The high frequency treatment instrument is provided with an insulative flexible sheath, an operation wire inserted in the flexible sheath so as to be movable along an axial direction of the operation wire in the flexible sheath, and a hook-like electrode attached to a tip of the operation wire. The hook-like electrode includes a rod-like part which is elongated in parallel with the axial direction along a line shifted from an axis line of the operation wire, and a hook part elongated from the rod-like part to cross the axis line of the operation wire.

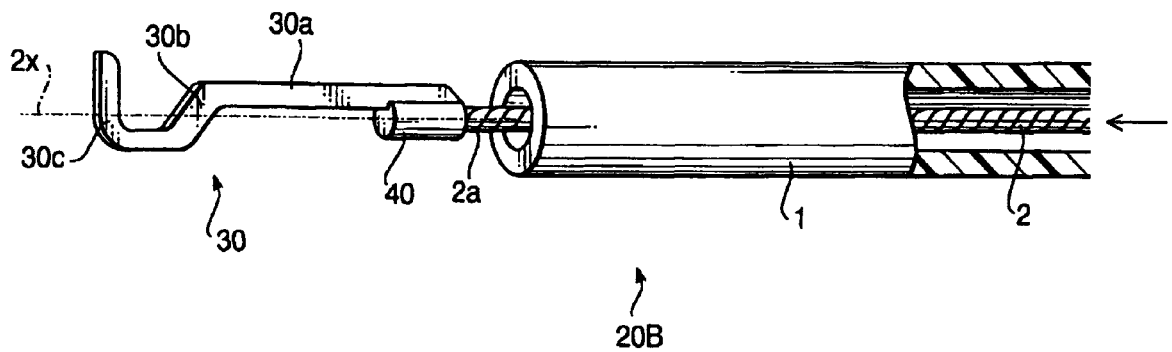

OTHER PUBLICATIONS

English language Abstract of JP 8-299355.
English language Abstract of JP 2002-153484.
English language Abstract of JP 5-293115.
English language Abstract of DE 10122731.
English language Abstract of De 3707820.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 1 is confirmed.

Claims 2-6 are cancelled.

New claims 19-24 are added and determined to be patentable.

Claims 7-18 were not reexamined.

*19. The high-frequency treatment instrument according to claim 1, wherein at least a tip portion of the flexible sheath comprises a flexible tube.*

*20. The high-frequency treatment instrument according to claim 1, wherein a shape of the hook-like electrode, upon retraction into the flexible sheath sheet is a same as the shape of the hook-like electrode upon extension from the flexible sheath.*

*21. The high-frequency treatment instrument according to claim 1, wherein a free end of the hook part comprises a return part that extends in a backward direction from a tip of the hook part.*

*22. The high-frequency treatment instrument according to claim 1, wherein a portion of the hook part between the part that extends straight from the tip of the slanting part and the part that extends in a lateral direction is curved so as to provide a mark forming surface.*

*23. The high-frequency treatment instrument according to claim 1, the hook line electrode being the attached to the operation wire at a position spaced from a longitudinal axis of the operation wire.*

*24. The high-frequency treatment instrument according to claim 1, the slanting part and the hook part together defining a generally U-shaped structure, both an inwardly facing edge surface and an outwardly facing edge surface of the U-shaped structure being configured to cut mucosa.*

\* \* \* \* \*